(12) United States Patent
Tharpe, Jr. et al.

(10) Patent No.: US 6,461,471 B1
(45) Date of Patent: Oct. 8, 2002

(54) DISPOSABLE UNDERGARMENT FORMING APPARATUS HAVING FOLDER REGISTRATION CONVEYOR SIDE CONNECTOR AND SEPARATOR

(76) Inventors: John M. Tharpe, Jr., 1005 Willie Pitts Jr., Rd. P.O. Box 3970, Albany, GA (US) 31706; Robert M. Herrin, 1005 Willie Pitts Jr., Rd., P.O. Box 3970, Albany, GA (US) 31706

( * ) Notice: Subject to any disclaimer, the term of this patent is extended or adjusted under 35 U.S.C. 154(b) by 0 days.

(21) Appl. No.: 09/417,291

(22) Filed: Oct. 13, 1999

Related U.S. Application Data

(60) Division of application No. 09/089,776, filed on Jun. 3, 1998, now Pat. No. 6,065,521, which is a continuation-in-part of application No. 08/667,518, filed on Jun. 21, 1996, now Pat. No. 5,879,500, and a continuation-in-part of application No. 09/020,452, filed on Feb. 9, 1998, now Pat. No. 6,116,317.

(51) Int. Cl.[7] .............................................. B32B 31/10
(52) U.S. Cl. ............................... 156/580.1; 156/580.2; 156/582
(58) Field of Search ................................. 156/204, 226, 156/227, 461, 580, 580.1, 580.2, 581, 582, 465, 553, 73.4

(56) References Cited

U.S. PATENT DOCUMENTS

| | | | |
|---|---|---|---|
| 3,758,364 A | * 9/1973 | Edelman | 156/463 |
| 4,089,728 A | 5/1978 | Teed | 156/352 |
| 4,650,173 A | 3/1987 | Johnson et al. | 270/45 |
| 4,650,530 A | * 3/1987 | Mahoney et al. | 156/73.1 |
| 4,750,955 A | * 6/1988 | Haguenier | 156/69 |
| 4,940,464 A | * 7/1990 | Van Gompel | 604/396 |
| 5,057,175 A | * 10/1991 | Ashton | 156/202 |
| 5,421,924 A | * 6/1995 | Ziegelhoffer et al. | 156/73.1 |
| 5,545,275 A | 8/1996 | Herrin et al. | 156/731 |
| 5,649,336 A | * 7/1997 | Finch et al. | 15/104.94 |

FOREIGN PATENT DOCUMENTS

| | | | |
|---|---|---|---|
| EP | 0 539 032 A1 | 4/1993 | 13/15 |
| WO | 97/34556 | 9/1997 | 13/15 |

* cited by examiner

Primary Examiner—Michael W. Ball
Assistant Examiner—Gladys Piazza
(74) Attorney, Agent, or Firm—Allen, Dyer, Doppelt, Milbrath & Gilchrist, P.A.

(57) ABSTRACT

An apparatus and method for forming a connection of portions of a moving folded web of disposable undergarments is provided. The apparatus preferably includes a registration conveyor positioned to register and convey a folded web of disposable undergarments moving along a predetermined path of travel and a web connector positioned adjacent the registration conveyor to connect portions of the folded web as the folded web is conveyed along the predetermined path of travel. A method preferably includes registeringly conveying a folded web of disposable undergarments along a predetermined path of travel and connecting portions of the folded web as the folded web is conveyed along the predetermined path of travel.

21 Claims, 6 Drawing Sheets

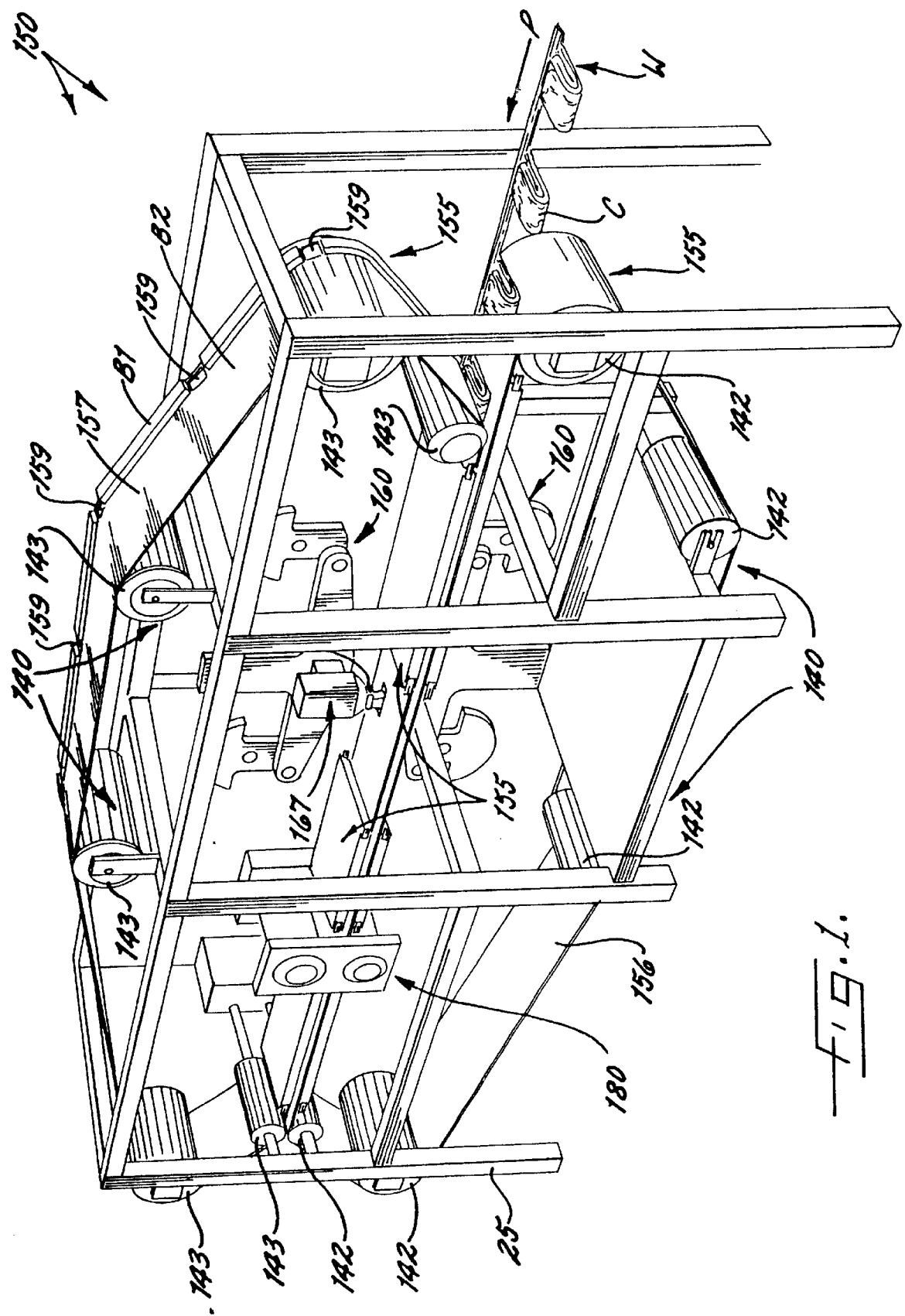

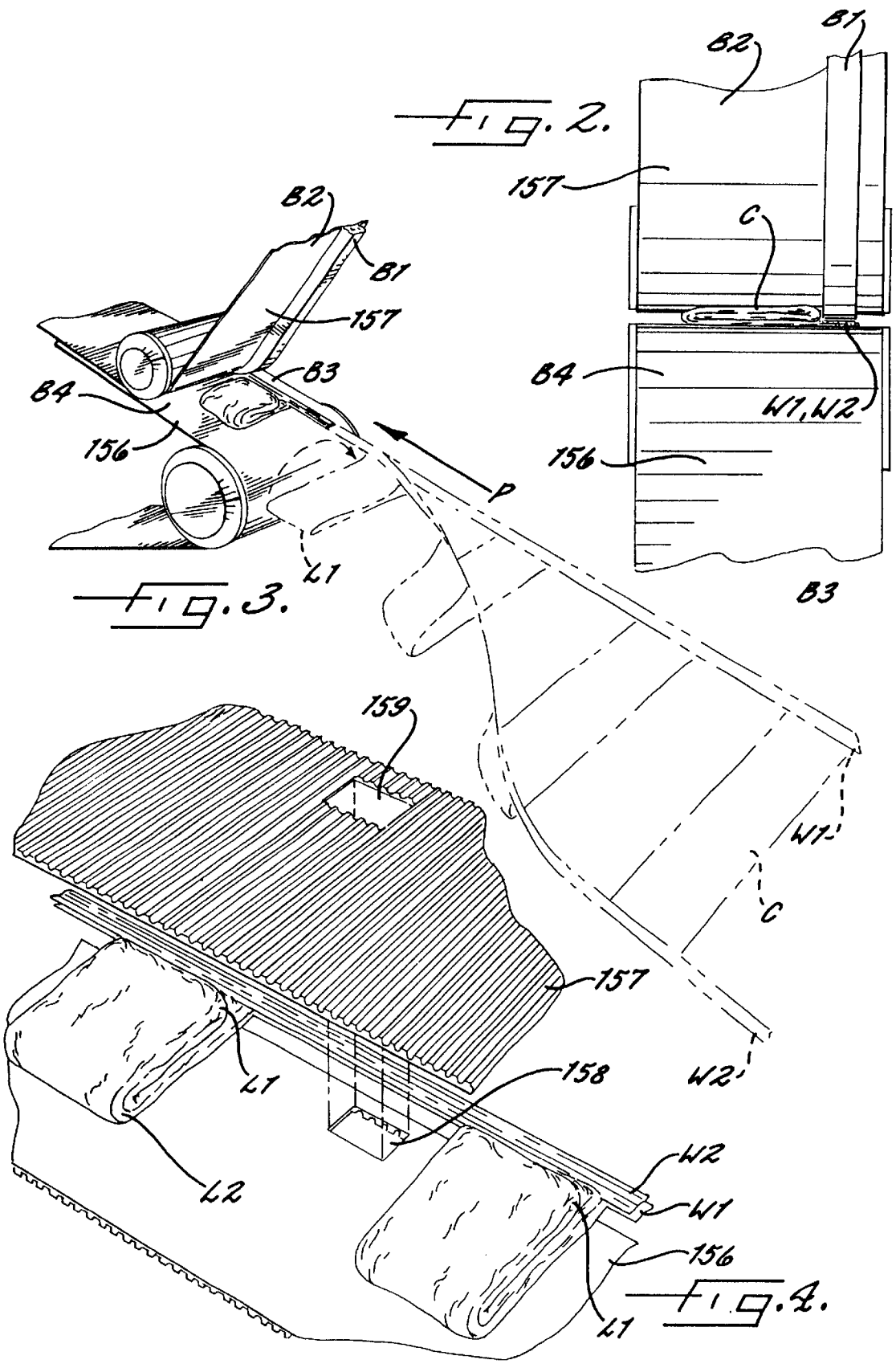

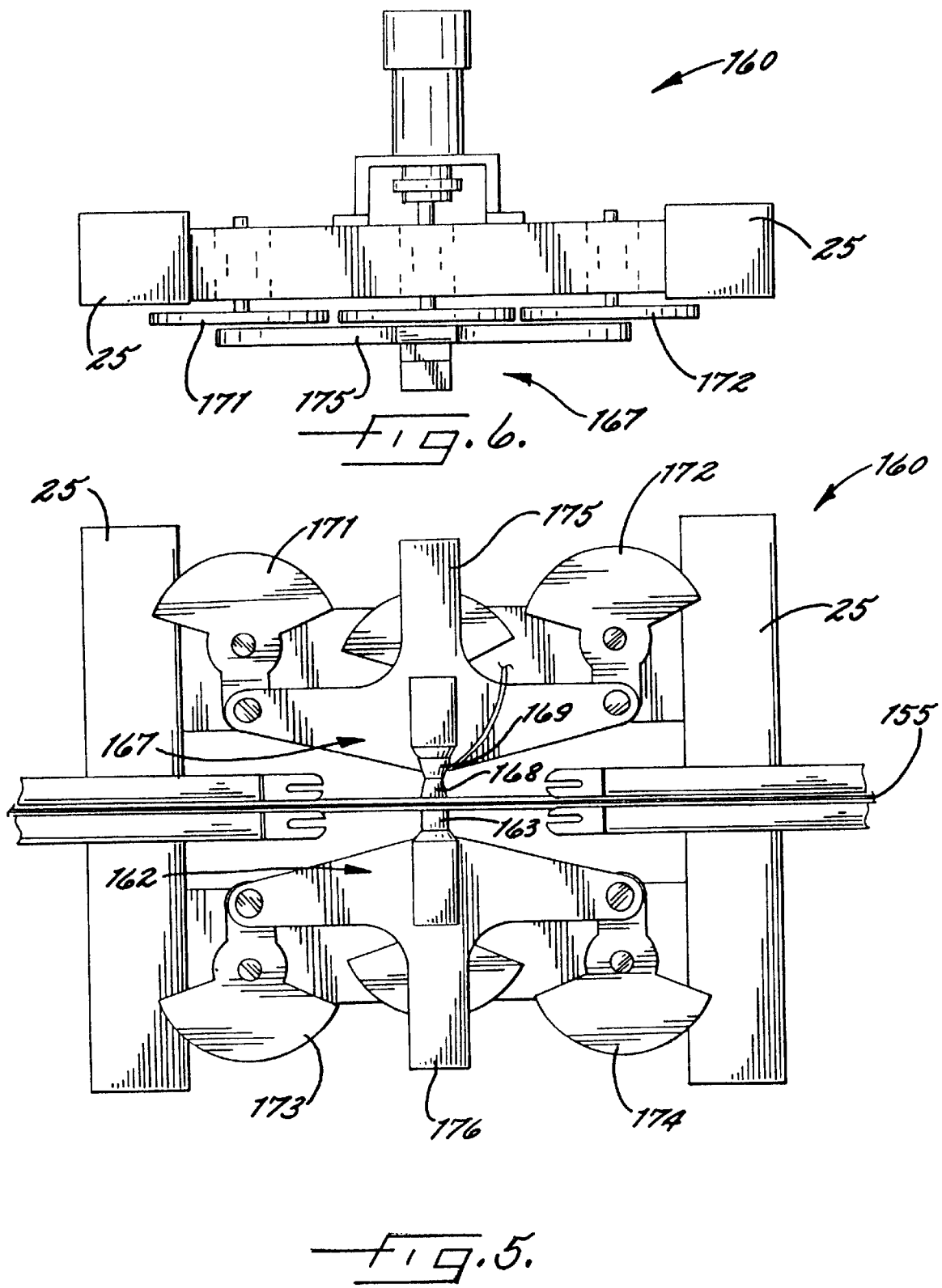

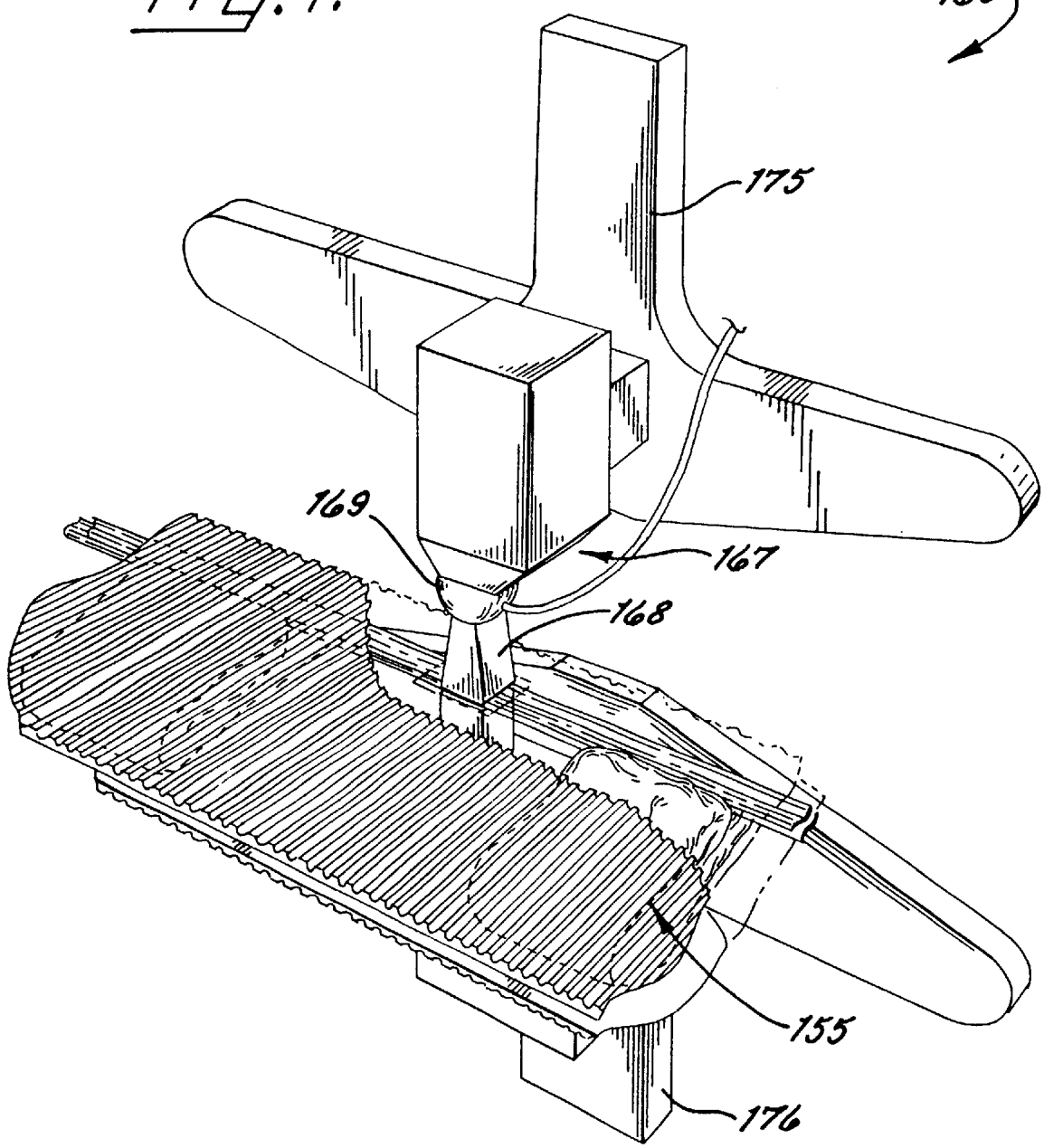

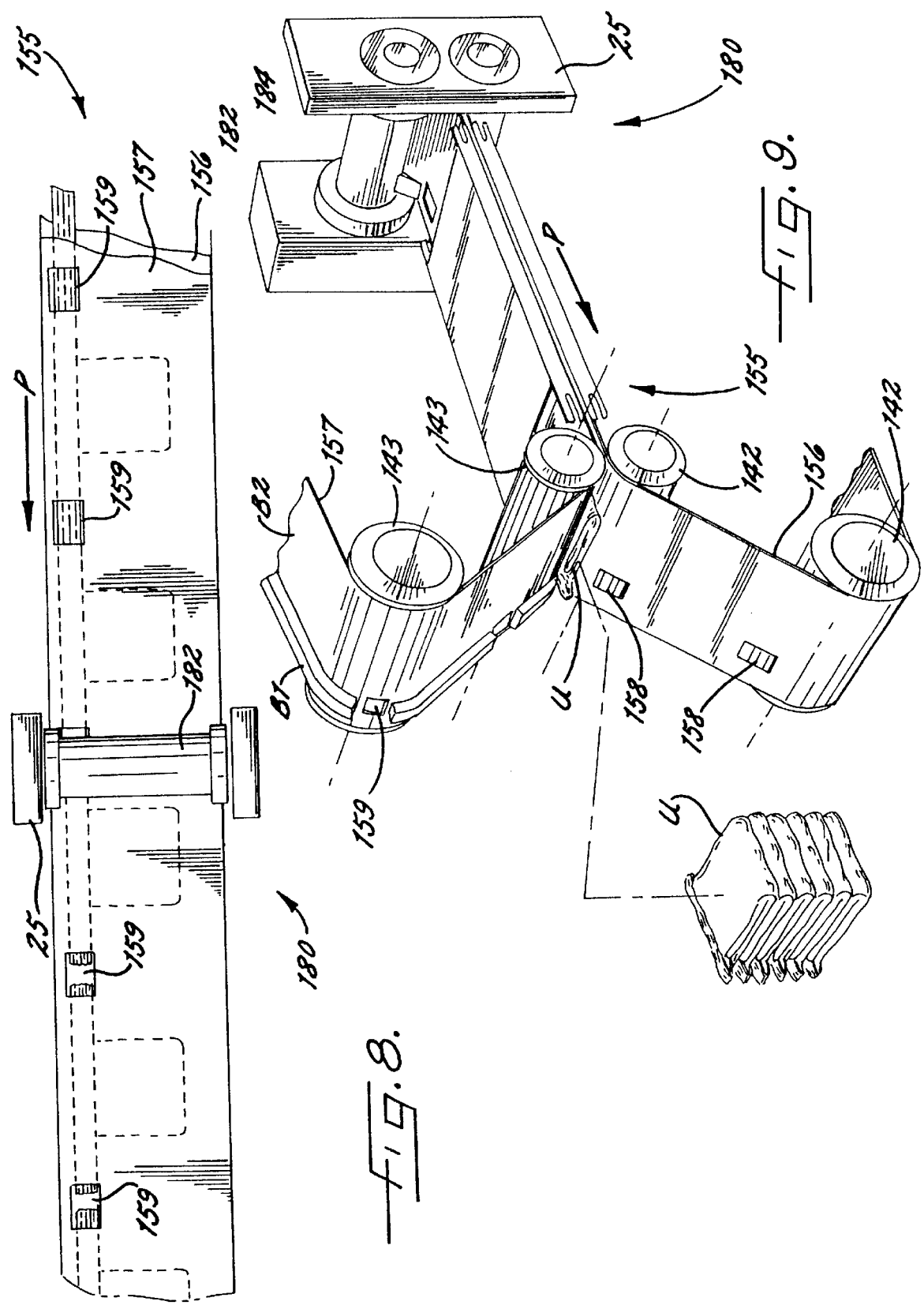

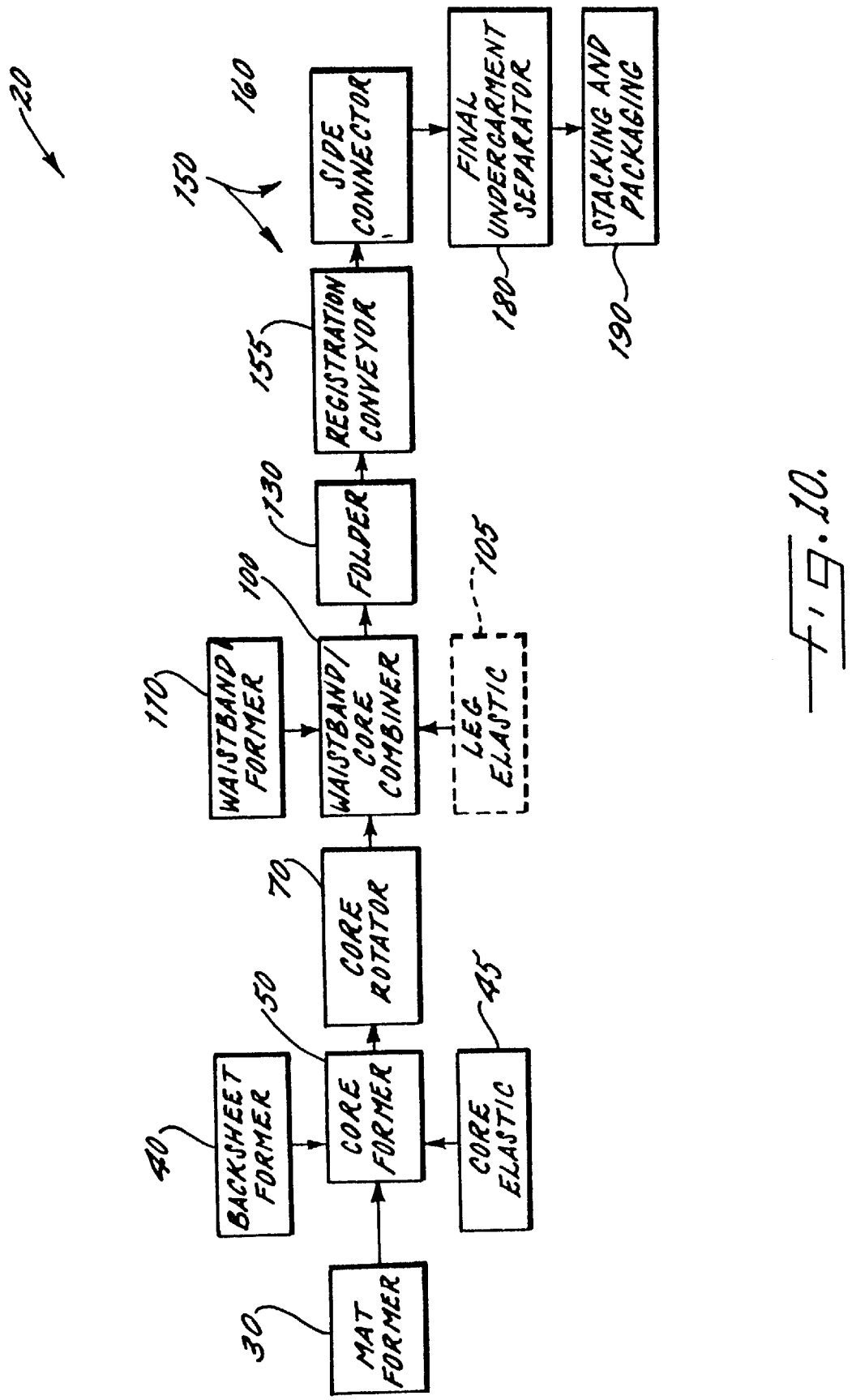

DISPOSABLE UNDERGARMENT FORMING APPARATUS HAVING FOLDER REGISTRATION CONVEYOR SIDE CONNECTOR AND SEPARATOR

RELATED APPLICATIONS

This patent application is a Division of U.S. Ser. No. 09/089,776, filed on Jun. 3, 1998, titled "Disposable Undergarment Forming Apparatus having Folder, Registration Conveyor, Side Connector, and Separator and Methods of Folding, Registering Conveying, Connecting, and Separating Same" is now U.S. Pat. No. 6,065,521 which itself is a continuation-in-part of U.S. patent application Ser. No. 08/667,518, filed on Jun. 21, 1996, which is now U.S. Pat. No. 5,879,500 and U.S. patent application Ser. No. 09/020,452, filed on Feb. 9, 1998, titled "Apparatus Having a Core Orientor And Methods of Orienting Portions of a Disposable Undergarment", which is now U.S. Pat. No. 6,116,317 and which are each hereby incorporated herein by reference in their entireties.

FIELD OF THE INVENTION

The invention relates to the field of disposable products, and, more particularly, to the field of disposable undergarments.

BACKGROUND OF THE INVENTION

Over the years, consumers have shifted demand from cloth diapers to disposable diapers for infants and toddlers. This demand has increased and developed the disposable diaper industry into a major industry. As this industry developed, consumers preferred and often demanded improvements in disposable products which included better core absorbency, products which are easier to fasten, detach, and reattach side peripheries of the waistbands, various sizes of products for various weights and sizes of infants and toddler, and better control of leakage from around the legs and waistbands when the diaper is positioned on an infant or toddler.

This development of the disposable diaper industry, however, has increased demand for faster and more efficient disposable undergarment production. This demand is further complicated by the development of disposable infant and toddler briefs, which have a different product configuration and have different product performance requirements than disposable diapers. Also, because of the relative success of the disposable diapers and the high volume of disposable diaper products produced in manufacturing, the market for toddler briefs has generally been a much smaller subset of the infant and toddler disposable diaper market. The demand for toddler briefs in general is substantially less than the disposable diapers. Accordingly, these specially configured briefs are not normally produced on the same production line as the disposable diaper production line. Because the market demand for these briefs is less, product manufacturers are less inclined to invest in additional machinery for producing these products. The product manufacturer, however, is also pushed by retailers and consumers to provide a full-line of disposable products for infants and toddlers.

Additionally, as the nursing home care and elderly care industry has grown over the years, the elderly often have needed more and more assistance from nursing home or elderly care personnel, including urination and bowel movement assistance. Urination and bowel movement problems have also arisen among various aged adults such as loss of bladder control through childbirth or other medical reasons. Therefore, because manufacturers of disposable undergarments can be limited in the foot-print or square footage available for production, especially for adult, toddler, and infant specialty undergarments such as briefs, and because labor costs can be quite expensive, demand continues to increase for systems which increase production speed of disposable undergarments in a relatively small amount of space.

SUMMARY OF THE INVENTION

In view of the foregoing background, the present invention advantageously provides an apparatus and methods for forming a connection of portions of a moving folded web of disposable undergarments. The present invention also advantageously provides a disposable undergarment forming apparatus having a folder, a registrations conveyor, a side connector, and/or a separator.

The present invention additionally advantageously provides an apparatus and method for registering and conveying a web of disposable undergarments. The present invention further provides a disposable undergarment forming apparatus and method of producing a plurality of disposable undergarments which increases the production speed and reduces the square footage of floor or manufacturing space needed for producing the disposable undergarments to thereby increase the value and productivity of a production line.

The present invention also advantageously provides a disposable undergarment forming apparatus and method for producing disposable undergarments more efficiently. The present invention further advantageously provides a disposable undergarment forming apparatus and method having the flexibility to produce both infant or toddler undergarments and adult undergarments and produce different undergarment configurations efficiently with only minor production line changes.

More particularly, the apparatus preferably includes registration conveying means for registering and conveying a folded web of disposable undergarments moving along a predetermined path of travel and web connecting means positioned adjacent said registration conveying means for connecting portions of the folded web as the folded web is conveyed along the predetermined path of travel.

The present invention also provides an apparatus for registering and conveying portions of a moving folded web of disposable undergarments. The apparatus preferably includes first web contacting means, e.g., provided by a first conveying belt, for abuttingly contacting portions of a folded web of disposable undergarments moving along a predetermined path of travel and second web contacting means, e.g., provided by a second conveying belt, positioned adjacent the first web contacting means for abuttingly contacting the folded web so that the first and second web contacting means cooperate to register and hold the folded web therebetween. The apparatus also preferably includes driving means positioned to contact the first and second web contacting means for driving the first and second web contacting means along the predetermined path of travel to thereby move or transport the folded web along the same predetermined path of travel.

The present invention additionally provides methods of forming a connection of portions of a moving folded web of disposable undergarments. A method preferably includes registeringly conveying a folded web of disposable undergarments along a predetermined path of travel and connecting portions of the folded web as the folded web is conveyed along the predetermined path of travel.

Another method for forming a connection of portions of a web of disposable undergarments preferably includes folding cores of a web of disposable undergarments during travel along a predetermined path, registeringly conveying the folded web of disposable undergarments along a predetermined path of travel, connecting portions of the folded web as the folded web is conveyed along the predetermined path of travel, and separating the folded web of disposable undergarments along the connected portions of the folded web so as to form a plurality of individual disposable undergarments.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 1 is a perspective view of an apparatus for registering, conveying, connecting, and separating portions of a web of disposable undergarments according to the present invention;

FIG. 2 is fragmentary front elevational view of a pair of belts of a registration conveyor of an apparatus for registering, conveying, connecting, and separating portions of a web of disposable undergarments according to the present invention;

FIG. 3 is a fragmentary perspective view of a pair of belts of a registration conveyor of an apparatus for registering, conveying, connecting, and separating portions of a web of disposable undergarments and includes the folding and side folding of the web prior to entry into the registration conveyor as shown in dashed lines according to the present invention;

FIG. 4 is an exploded fragmentary view of a pair of belts of a registration conveyor of an apparatus for registering, conveying, connecting, and separating portions of a web of disposable undergarments according to the present invention;

FIG. 5 is a side elevational view of an apparatus for folding, registering, conveying, connecting, and separating portions of a web of disposable undergarments according to the present invention;

FIG. 6 is a top plan view of a side connector of an apparatus for folding, registering, conveying, connecting, and separating portions of a web of disposable undergarments according to the present invention;

FIG. 7 is a fragmentary perspective view of an apparatus for folding, registering, conveying, connecting, and separating portions of a web of disposable undergarments according to the present invention;

FIG. 8 is a top plan view of a registration conveyor and a separator of an apparatus for folding, registering, conveying, connecting, and separating portions of a web of disposable undergarments according to the present invention;

FIG. 9 is a perspective view a registration conveyor and a separator of an apparatus for folding, registering, conveying, connecting, and separating portions of a web of disposable undergarments according to the present invention; and FIG. 10 is a block diagram of a disposable undergarment forming apparatus having a folder, a registration conveyor, a side connector, and a separator according to the present invention.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and double prime notation, if used, indicate similar elements in alternative embodiments.

FIG. 10 schematically illustrates an overview of a disposable undergarment apparatus 20 and method for forming a plurality of disposable undergarments according to the present invention. FIG. 10 will be referenced throughout this description as an overview for other more specific elements and operational aspects described throughout. The apparatus 20 preferably includes a frame 25 (see portions thereof illustrated in FIG. 1), including a plurality of frame members, and core forming means, e.g., a core former 50, mounted to the frame 25 for forming a stream or a sheet S of a plurality of elongate undergarment cores C traveling along a path of travel P generally indicated by the flow arrows (see FIGS. 1, 3 and 8–9). The cores C, as well as other portions of undergarments U, preferably are conveyed or driven along the path of travel P by various conveyors which include respective conveyor drives of the apparatus 20 as understood by those skilled in the art. The apparatus 20 preferably also includes control means, such as one or more controllers, which can advantageously be connected to the conveyors, including a registration conveyor 155, and the various other portions of the apparatus 20, including a folder 130, a side connector 160, and a final undergarment separator 180, described further herein for controlling various stages of the undergarment forming apparatus 20 during the formation and production of undergarments U. The controllers, e.g., controllers 162, 192, preferably are microprocessor or other computer based controls and can include a plurality of optical encoders as understood by those skilled in the art.

As also illustrated in FIG. 10, mat forming means, e.g., a mat former 30, is positioned upstream from the core forming means 50 for forming a mat for each of the cores C produced by the apparatus 20. The mat former 30, as understood by those skilled in the art, preferably includes a feeder for feeding a super absorbent polymer ("SAP") and a pulp source. The pulp source preferably includes rolled pulp mounted on pulp feed rolls and a pulp grinder for grinding the pulp. The SAP and pulp are fed to a forming chamber where the pulp is mixed with the SAP to form a stream or continuous flow of bulked mat material at a mat material former. The mat material of the mat forms a significant part of the core C of an undergarment and assists in forming an absorbent portion of the core C for collecting moisture such as urination from an adult or infant. A sheet of tissue from a tissue source is preferably positioned to underlie the bulked mat material, and the combination is conveyed by a debulking conveyor to a debulker. The tissue can also be positioned to underlie the mat material and wrapped around, e.g., so as to overlie, the mat material as well. From the debulker, the debulked stream of mat material is embossed by an embosser and cut into a plurality of individual mats by a mat knife or mat separator positioned downstream from the embosser.

The individual mats are then intermittently-spaced and conveyed by a conveyor along the path P of travel to the core forming means 50. The core forming means 50 of the apparatus 20 preferably includes mat securing means, e.g., a mat/backsheet combiner, for securing a lower surface of each of the plurality of intermittently-spaced elongate undergarment mats to an upper surface of a sheet, e.g., backsheet, of a polymeric material traveling along the path of travel P so that side lengthwise peripheries of the intermittently-spaced elongate undergarment mats are positioned generally parallel to side lengthwise peripheries of the polymeric sheet. The polymeric core backing sheet is preferably supplied by a sheet source or backsheet former 40 such as a wound roll of the polymeric sheet material mounted on feed rolls. The undergarment mats are preferably secured to the polymeric backing sheet by an adhesive material such as glue from an adhesive applicator. Such adhesive applicators as described and referenced in various positions herein will be understood by those skilled in the art.

Core elastic applying means, e.g., a core elastic applicator 45 (FIG. 10), is positioned downstream from the mat securing means for applying strips of elongate elastic material to the upper surfaces of the side lengthwise peripheries of the polymeric sheet adjacent and generally parallel to the intermittently-spaced elongate undergarment mats. The core elastic applicator 45 preferably includes a source of core elastic, a feeder for feeding the core elastic to the polymeric backing sheet, and an adhesive applicator for applying adhesive to either the backing sheet or the core elastic to thereby secure the core elastic to the backing sheet.

The core forming means 50 can also further include stand-up leg gather forming means, e.g., a stand-up leg gather ("SULG") former, positioned adjacent the core elastic applying means for forming stand-up leg gathers on the polymeric sheet, as understood by those skilled in the art, which inhibit liquid, such as from urination, from leaking from the legs of the undergarment U. Although various single-piece, three-piece, and other configurations of a SULG, as understood by those skilled in the art, can be formed by the apparatus 20 of the present invention, the stand-up leg gather forming means according to the present invention preferably includes leg sealing means, e.g., a sealer, for sealing polymeric material so as to form a liquid impervious seal around each of the SULGs of the plurality of cores C. The sealer preferably is an adhesive or heat seal applied between the layers of polymeric material. The seal, e.g., heat or adhesive, is preferably formed between the SULG polymeric material and the polymeric backing sheet to inhibit leakage of moisture or liquid from and around the mat material and legs.

The SULGs, for example, can be formed by a first sheet of polymeric material supplied from a SULG polymeric sheet source, a plurality of elongate elastic strips supplied from a SULG elastic source, and a top sheet of non-woven material supplied from a top sheet non-woven sheet source. The sheet of SULG polymeric material is divided into two strips, one for each leg. A first set of strips, e.g., one or more strips, of elastic material is positioned to extend adjacent a lengthwise side periphery of the backing sheet, and each strip of polymeric material is positioned to overlie the first set of elastic strips and extend between the lengthwise side periphery and the mat material. The seal between the polymeric sheet material as described above is formed.

The non-woven sheet material overlies and adheres to the polymeric material along each leg, but also overlies the mat material of the core C. A second set of elastic strips, e.g., one or more elastic strips, are also positioned along peripheries of each of the SULG polymeric strips adjacent the mat material. These elastic strips preferably are positioned between the non-woven sheet material and the polymeric strip. These first and second sets of elastic strips preferably are applied to the surface of the backing sheet in an extended position so that when the strips are relaxed or retracted, the backing sheet, the SULG polymeric strips, and the non-woven sheet gather or form gathers extending lengthwise along what will become the legs of the core C. This, for example, allows the SULGs which eventually become the SULGs of the undergarments to be stretched when positioning the undergarment on a user to thereby provide a snug and comfortable fit around the legs of a user when relaxed or retracted. The portion of the SULG polymeric strips, the second set of elastic strips, and the portion of the non-woven sheet adjacent lengthwise peripheries of the mat material are formed to extend upwardly away from the upper surface of the mat material and the backing sheet as illustrated.

The core forming means 50 also includes first separating means, e.g., a core separator such as a knife or blade, positioned downstream from the core elastic applying means for separating the stream of intermittently-spaced elongate undergarment cores C into a plurality of individual undergarment cores C. The core separator preferably is a knife mounted to a drum cylinder or roll having a predetermined circumference and which overlies and periodically contacts the stream of cores C. The knife extends the length or height of the drum cylinder so as to form a relatively small cutting line. The drum cylinder is mounted to rotate so that during one rotation cycle the knife cuts the stream of cores C only one time to thereby produce a plurality of individual cores C during a corresponding plurality of rotations. It will be understood by those skilled in the art, however, that other core separator configurations could be used as well such as multiple blades on a larger drum cylinder.

Additionally, as illustrated in FIG. 10, the apparatus 20 also includes an orienting apparatus 70 for orienting a plurality of portions, e.g., cores, waistbands, leg gathers, backing sheets, or respective portions thereof, of web of a plurality of disposable undergarments. Because the core C of a disposable undergarment can require extensive forming, preparing, and handling operations, e.g., due to the absorbency or super-absorbency nature of the core of a disposable undergarment as described herein above, the orienting apparatus 70 of the present invention can advantageously be and is preferably used for orienting a core C of a disposable undergarment. The orienting apparatus 70 preferably includes lifting means for lifting each of a plurality of cores C for forming a web W of disposable undergarments when in a first orientation position during travel along a predetermined path P or direction of manufacture and orienting or core orienting means connected to the lifting means for orienting each of the plurality of cores in a second orientation position along the predetermined path of travel P. The core orienting means preferably includes driving means for driving the lifting means along the predetermined path of travel P and orientation changing means associated with the driving means for changing the orientation of each of the lifted cores C to the second orientation position when driving the lifting means along the predetermined path of travel P. The orientation changing means, for example, preferably includes means for driving portions of the lifting means along first and second driving paths. The second driving path is preferably positioned to generally overlie the first driving path and to direct a second portion of the lifting means along a different path of travel than a first portion traveling along the first driving path.

The orienting apparatus 70, e.g., including a core orientor, is preferably positioned downstream from the core forming means 50 for orienting, e.g., preferably by rotating each core C about 90 degrees, each of the plurality of individual elongate undergarment cores C to a position having a lengthwise extent of the cores C transverse the path of travel P. The core orientor or rotator 70 preferably lifts the individual cores C from the surface of the conveyor, orients by rotating each of the cores C to a position transverse the path of travel P, and then releases each of the cores C for other downstream operations. The lifting of each of the cores C is preferably performed by a vacuum or suction system which defines core holding means for holding a core C in a suspended position after lifting the core C off of a surface and for releasing the core C from the suspended position and can operatively accommodate the lifting and rotating of a plurality of cores C and inoperatively release the cores C therefrom so that the production line operation continues in a smooth process.

The vacuum or suction system preferably includes a vacuum chamber forward in a suction delivery channel having a vacuum source connected thereto by a plurality of hoses and a plurality of core lifters or lifting members arranged so that a suctioning interface member, a flexible suction cup or annular flexible flange, of each of the core lifters or lifting members abuttingly contact and are in fluid communication with the vacuum chamber. The vacuum chamber provides the vacuum lift or holding means for each of the plurality of lifters when the lifters are in contact with the vacuum chamber.

The plurality of lifters preferably are mounted to drive means, e.g., a pair of closed-loop chain drives, a plurality of drive gears for contactingly driving each of the pair of chain drives, and at least one motor for driving each of the plurality of drive gears, so as to rotate around the first and second drive paths. Each lifting member includes a pair of mounting arms connected to the drive means and a core plate member or platen mounted to one of the pair of mounting arms. The platen preferably is arranged to be positioned so as to overlie an individual core C for lifting and abuttingly contacting the core C for orientation when the suction interface member contacts and is in fluid communication with the vacuum chamber. A first arm is connected to the platen and has a second arm pivotally or rotatingly connected thereto. The second arm has an end thereof which pivotally connects to the first arm and extends outwardly therefrom.

The first arm is also somewhat fixedly connected to a first portion of the driving means, e.g., a first chain drive. The second arm is slidably and pivotally connected to a second portion of the driving means, e.g., a second chain drive. The first and second chain drives are also mounted to portions of the frame 25. The second chain drive also preferably includes a drive chain, a plurality of gears drivingly connected to the drive chain, and at least one motor or a connection to the other motor for driving the gears.

The second arm also advantageously includes an elongate slot positioned to receive a slot following pin therein. The pin connects to the second chain drive and slides along or follows the slot when the lifter moves along the first and second drive paths. This structure, in essence, defines an adjustable compensating means for compensating for the differences in the drive paths which provide orientation or rotation of the platen of each of the lifters. In other words, the slidable movement of the following pin within the slot of the second arm assists during the slowing down of the movement of the pin in comparison to the constant movement of the first arm and platen along the first drive path by the changing of the phase angle based upon the sine or cosine. The second chain drive is preferably positioned for driving the second arm along a different path of travel than the first chain drive which drives the first arm along a predetermined path of travel. Notably, the lifters continuously travel along a closed loop path of travel when being driven by the first and second chain drives.

Also, the first arm of each of the plurality of lifters preferably includes a substantially hollow interior portion extending a selected length of the first arm. The platen also has a plurality of openings formed therein and positioned in fluid communication with the substantially hollow portion of the first arm connected thereto. The suctioning interface member is connected to the first arm and also in fluid communication with the substantially hollow portion of the first arm. When suction or a vacuum is applied to the suctioning interface member when each lifter travels along the predetermined path adjacent the conveyor, the suction extends through the suctioning interface member from the elongate vacuum or suction delivery channel, e.g., by slidable engagement with the opening of the channel, through the substantially hollow interior portion of the first arm, and through the plurality of openings in the platen for lifting a core C when positioned on a surface of the conveyor adjacent the platen. The conveyor also can have a vacuum or suction from the vacuum or suction system applied thereto for assisting in inhibiting slippage or movement of the cores C positioned thereon.

Each lifter or lifting member is arranged for rotating the core C from the position having a lengthwise extent travelling in the direction of the path of travel P to the position transverse the path of travel P. Upon reaching a predetermined position, the lifting member releases the core C and continues to rotate around the first and second drive paths so as to return for lifting another core C in the production process.

The orienting or rotating of the cores C so as to have lengthwise extents transverse the path of travel P allows for the disposable undergarment forming apparatus 20 to have a reduced number of and a more narrow glue or adhesive application path for one or more glue or adhesive applicators to secure the waistbands W1, W2 to the cores C downstream. The glue or adhesive is preferably applied before rotation of the cores C. It can also allow for a reduced amount of adhesive to be used for each undergarment and thereby reduce the production costs associated with each undergarment.

Elastic waistband forming means, e.g., a waistband former 110, preferably is positioned adjacent the core rotating means 50 and positioned to form at least two continuous strips of elongate elastic material extending along the path of travel P for forming elongate elastic waistbands W1, W2. The waistband forming means preferably is formed "off-line" from the path of travel P for ease of modifying the type of waistband that can be used for a given product. It will be understood by those skilled in the art, however, that the waistband forming means 110 can also be positioned "in-line" as well. The waistband forming means 110 includes dividing means, e.g., a sheet divider as understood by those skilled in the art, for dividing a continuous sheet of non-woven material supplied from a non-woven sheet source into the plurality of continuous strips and strip combining means e.g., a strip combiner, for combining strips of elastic material from a waistband elastic supply source with the plurality of continuous strips of non-woven material.

The plurality of continuous strips as described above preferably includes four strips of non-woven material. These four strips form two pairs of continuous waistband strips W1, W2. Each waistband strip W1, W2 has an upper and a lower non-woven strip and one or more, e.g., preferably four, elastic strips positioned therebetween. Two of the four non-woven strips preferably have greater widths than the other two non-woven strips. These two greater width non-woven strips preferably form the lower non-woven strips of the two pairs of continuous waistband strips. The one or more elastic strips preferably are only adhered to a medial portion of the lower non-woven strips so that lengthwise periphery portions of the lower non-woven strips remain unelasticized. After the upper and lower non-woven strips and the elastic strip(s) are combined, one of the non-elasticized lengthwise periphery portions of each upper non-woven strip is folded by a folding guide member so as to now overlie and adhere to at least lengthwise peripheries of the upper non-woven strip. This fold, for example, will provide a smooth closure or sealed surface to the waistband strips W1, W2 and will eventually downstream become the lower portion of the waistband of the undergarment as described further herein.

The one or more elastic strips preferably are adhered to and positioned between the upper and lower non-woven strips, as well as the waistband strips W1, W2 being adhered to the individual cores as described further herein, in an extended position so that when released to the retracted or relaxed position, the waistband strips W1, W2 have a plurality of gathers formed therein. This, for example, allows the waistband strips W1, W2 which eventually become the waistbands of the undergarments to be stretched when positioning the undergarment on a user to thereby provide a snug and comfortable fit to the waist of a user when retracted or relaxed.

Combining means, e.g., waistband/core combiner 100, is positioned downstream from the core forming means 50 and is positioned to receive the two continuous waistband strips W1, W2 of elongate elastic material from the elastic waistband forming means 110 along the path of travel P for respectively combining each of the two elongate elastic strips of material so as to be secured to, e.g., by using a glue or other adhesive, the respective side peripheries, e.g., lateral or widthwise sides, of each of the plurality of individual undergarment cores C traveling transverse to the path of travel to thereby form a chain of a plurality of undergarments U joined by the elongate elastic waistbands W1, W2. The combiner 100 preferably includes a plurality of feed and/or draw rolls positioned to cooperate with a conveyor which conveys the transversely positioned cores along the path of travel P. The rolls preferably feed or draw the waistband and, optionally, leg elastic to combine with the cores.

The lateral or widthwise peripheries of each individual core C preferably is glued or adhesively applied to the spaced-apart pair of waistband strips W1, W2 of the combiner. The lateral peripheries of each core C preferably are initially secured to the waistband strips W1, W2 so as to overlie the waistband strips W1, W2. As will be described further herein, the greater widthwise lower strips of the waistband strips W1, W2 are later folded so that portions of what was designated as the lower non-woven strip now overlie the lateral side peripheries of the core and what was designated as the upper non-woven strip.

A leg elastic source 105, according to another embodiment of the present invention, can supply additional leg elastic at this stage of the production process, or further upstream, for combining with and into the waistband/core combiner 100. The leg elastic is preferably adhered to the lengthwise peripheries of each of the plurality of cores adjacent the SULGs in an extended position so that when the leg elastic is released to a retracted or relaxed position gathers are formed around these lengthwise peripheries. This, for example, allows the leg gathers which eventually become the legs of the undergarments to be stretched when positioning the undergarment on a user to thereby provide a snug and comfortable fit around the legs of a user when relaxed or retracted.

Additionally, folding means is positioned downstream from the combining means 100 for folding each of the plurality of undergarments U of the web W or chain. The folding means, e.g., preferably provided by a folder 130, includes a waistband folder for folding the pair of continuous waistband strips W1, W2 of material forming the waistbands W1, W2 of the web W. The waistband folder 130 preferably includes waistband guide members which fold portions of the lower non-woven strip which do not have elastic adhered thereto so as now to overlie the upper non-woven strip and lateral peripheries of each individual core C. This waistband folder 130 thereby forms both a waistband seal and a smooth inner surface for interfacing with or abuttingly contacting the waist of a user.

The folder 130 also has a core folder positioned downstream from the waistband folder for bi-folding each of the cores c of the plurality of undergarments U of the web W along a predetermined core fold line L1 so that the two continuous strips of waistband material W1, W2 are positioned adjacent and in close relation to each other (see FIG. 3). The core folder, e.g., a first or primary core folder, preferably includes a core folding guide member which abuttingly contacts each of the plurality of individual cores which now have the lengthwise extents thereof travelling in a transverse direction to the path of travel P. The core folder preferably also includes a first compressor positioned downstream from the core folding guide member for compressing the core after it has been folded.

The folder 130 further has an undergarment second core folder, e.g., a side folder, positioned downstream from the core folder for folding each of the bi-folded cores of the plurality of undergarments U of the web W a second time along another predetermined core fold line L2. The side folder, or secondary folder, preferably includes a roller guide member and a belt member cooperating with the roller guide member which guide the lower extending peripheries of the bi-folded core upwardly so as to now be positioned adjacent the waistband strips W1, W2 as illustrated in FIG. 3. The side folder preferably also includes a second compressor preferably positioned downstream from the roller guide and the belt member for compressing the core after the second or side fold. Although the side folder is applicable to all types of garments, it is particularly applicable to adult undergarments which generally include cores having a greater lengthwise extent than those for infants or toddlers. The side folder, for example, allows the core to be folded to a more compact position for handling, stacking, and/or packaging further downstream. An example of the folding means 130, including the waistband folder, the core folder, and the side folder, are perhaps best illustrated in co-pending U.S. patent application Ser. No. 08/667,518 which is now U.S. Pat. No. 5,879,500 and which is hereby incorporated herein by reference in its entirety.

Also, side connecting means, e.g., including a side connector 150, is positioned downstream from the folding means 130 for intermittently connecting at least portions of the two continuous strips of waistband material W1, W2 extending between each of the plurality of cores C of the plurality of undergarments U of the web W to form side peripheries of individual undergarments U. The side connecting means 150 preferably includes registration conveying means, e.g., a registration conveyor 155, positioned downstream from the folding means for receiving, registering, e.g., aligning, holding and/or clamping, and conveying the folded web W of the plurality of undergarments U to and through a side sealer 160 and to and through second separating means, e.g., a final knife or an undergarment separator 180.

As perhaps best illustrated in FIGS. 1–4, the registration conveying means 155 preferably includes a first underlying conveying belt 156 positioned to underlie the folded web W and a second overlying conveying belt 157 positioned to overlie the folded web. The registration conveyor 155 also includes driving means 140, e.g., at least one drive, cooperating with each of the belts 156, 157 along the predetermined path of travel P. The driving means 140 preferably includes at least one motor, and preferably a plurality of motors, for driving a plurality of drive rolls 142, 143. The drive rolls 142, 143, in turn, interface with and contactingly drive the belts such as illustrated in FIG. 1.

Additionally, at least one of the conveying belts, e.g., a second overlying belt 157, has a first portion B1 having a first thickness and a second portion B2 having a second thickness. The first thickness is preferably greater than the second thickness. The first underlying conveying belt 156 also has corresponding portions B3, B4 which, however, can both be of generally the same thickness as the second portion B2. The combination of the first portion B1 of the second belt 157 and the corresponding first portion B3 of the first belt 156 is positioned to register and convey a waistband region of the folded web W. The combination of the second portion B2 of the second belt 157 and the corresponding second portion B4 of the first belt 156 is positioned to register and convey a core region C of each undergarment of the folded web W, e.g., so that each of the undergarments of the web are sandwiched, clamped, and registered between the belts.

It will be understood by those skilled in the art that the registration conveyor of the present invention can have the belts and thicknesses of the belts arranged in different configurations according to the present invention. For example, alternatively, the belts can also advantageously have less thick portions for positioning the folded undergarment therein and thicker portions in regions between the folded undergarments. This configuration can advantageously allow control of desired spacing between the undergarments and can work in combination with the side sealer as described further herein to synchronize the movement of one or more side sealers, e.g., horn and anvil assemblies as described. This configuration further advantageously further restricts or inhibits movement of the folded undergarment once the undergarment is positioned therebetween.

Also, the first conveying belt 156 travels along a closed loop path so that a first portion, e.g., a horn assembly, of web connecting means, e.g., a side connector 160, is positioned within the general closed loop path of the first conveying belt 156 (see FIG. 1). Likewise, the second conveying belt 157 also travels along a closed loop path so that a second portion, e.g., an anvil assembly, of the web connecting means is positioned within the closed loop path of the second conveying belt 157. The first and second conveying belts 156, 157 each include at least one opening 158, 159, and more preferably a plurality of openings, formed therein. A first opening 158 of the first conveying belt 156 is preferably positionally aligned with a first opening 159 of the second conveying belt 157 so as to define an open region so that portions of the folded web W being registered and conveyed by the registration conveyor 155 extend within the open region.

The web connecting means is preferably positioned adjacent the registration conveyor 155 (see FIGS. 1 and 7) for abuttingly contacting portions of the web connecting means, e.g., a horn 163 and an anvil 168, with the moving folded web positioned in the open region of the registration conveyor 155. This abutting contact, in turn, connects the portions of the moving web positioned in the open region. These plurality of openings 158, 159 in the belts 156, 157 are preferably spaced apart at intervals corresponding to the spacing for connecting and separating the web W into individual undergarments U. Separating means, as described further herein, is also positioned adjacent the registration conveyor 155 for separating the portions of the moving web W positioned in the open region of the registration conveyor.

As perhaps best illustrated in FIGS. 1 and 5–7, the side sealer 160 of the side connecting means 150 preferably provides the web connecting means and preferably is connected to the frame 25 and is positioned to ultrasonically and connectively seal the intermittent portions of the waistband material of the folded web W as the undergarments are being conveyed. The side sealer 160 preferably includes a lower crank mounting assembly 161 including a horn assembly 162 having a horn 163 rotatably mounted on the frame 25 along one side of the path of travel P. The side sealer 160 also has an upper crank mounting assembly 166 including an anvil assembly 167 rotatably mounted on the other side of the path of travel P and positionally aligned with the horn assembly 162 so as to seal or clamp opposing portions of the waistband strips W1, W2 together for sealing thereof. Other examples of such a horn assembly and an anvil assembly are also illustrated and described in co-pending U.S. patent application Ser. No. 07/884,804 filed on May 19, 1992, now abandoned, and which is hereby incorporated herein by reference.

More particularly, the side connector 160 can include driving means, e.g., preferably provided by a side connector drive 170, according to the present invention. The side connector 160 also can include the ultrasonic side sealer which has the horn assembly 162 and the anvil assembly 167. The driving means, e.g., a side connector drive 170, is preferably connected to the side sealer for reciprocally driving the side sealer along the path of travel P. The drive 160 preferably includes a motor, e.g., a servo-motor as understood by those skilled in the art, connected to the frame 25 and the upper lower and upper crank assemblies 161, 166 each connected to the motor. As understood by those skilled in the art, the crank assemblies 161, 166 rotate corresponding to the rotation of a drive shaft and belt connected to the motor. The crank assemblies 161, 166 each preferably includes a pair of bar links 171, 172, 173, 174 connected to a main shuttle member 175, 176 and connected to a portion of the side sealer 160 as illustrated. The drive 170 preferably drives the side sealer 160 along the path of travel P, e.g., upstream and downstream, as indicated by the arrows and is preferably controlled and synchronized so that the side sealer 160 is driven downstream at a speed synchronous to the speed of the registration conveyor 155 having the folded web W of undergarments U positioned thereon. It will also be understood by those skilled in the art that multiple side sealers, e.g., horn and anvil assemblies, can be used as well according to the present invention. These multiple side sealers can advantageously be positioned on the same crank arm or different crank arms, but are preferably synchronized in their movement.

Each of the horn and anvil assemblies 162, 167 preferably connect to lower and upper shuttle members 175, 176 which load and unload or open and close the respective assemblies 162, 167 during operation. An air control system preferably controls a separate air bladder 169 or bladders of the anvil assembly 167. By use of the inflatable bladder 169, the anvil 168 is imparted with a significant degree of flexibility or compressibility which thereby permits the horn 163 and the anvil 168 to be in contact with each other for a much greater period of time during movement of the undergarment web W through the side sealer 160 along the path of travel P.

After each of the main shuttle members 175, 176 and the horn and anvil assemblies 162, 167 are positioned upstream and begin to move downstream at a speed synchronized with the speed of the registration conveyor 155, the horn 163 and the anvil 168 close and hold side periphery portions of the waistband material, e.g., pair of strips of waistband material W1, W2 (see FIG. 7). The assemblies 162, 167 are energized to provide ultrasonic energy to the material positioned between the horn 163 and the anvil 168. The material melts and the ultrasonic energy is stopped. The horn 163 and anvil 168, however, remain closed so that the material positioned therebetween will cool and resolidify to thereby form a seal or bond between the pair of strips of waistband material W1, W2.

As best illustrated in FIGS. 1 and 8–9, the disposable undergarment forming apparatus 20 also includes second separating means, e.g., an undergarment separator 180, is positioned downstream from the side connecting means 160 for separating the connective seal of the portions of the continuous strips of waistband material of the folded web W into a plurality of individual disposable undergarments U. The second separating means is preferably a rotating cylinder 182 or drum having a blade 184 or a final knife fixedly mounted thereto and arranged to periodically cut the web W of the plurality of undergarments U during rotation of the cylinder 182. It will be understood by those skilled in the art, however, that other undergarment separator configurations, as well as the other separators described herein, could be used as well, including various blade configurations, optical configurations (e.g., laser), and wire-type cutter configurations. The driving means 170 of the side connector 160 preferably is electrically connected to and tracks with or is synchronized with the undergarment separator 180 so that the position and timing for cutting or separating the folded web W into individual undergarments U advantageously occurs at the right time and position on the seal of the waistband material.

Further, as illustrated in FIG. 10, the apparatus 20 includes stacking and packaging means 190 is positioned downstream from the undergarment separator 180 for stacking and packaging the individual undergarments U produced. The stacking and packaging means 190 preferably includes position orientating means, e.g., a position orientor, positioned downstream from the second separating means 180 for positionally orienting the plurality of individual undergarments U from a generally vertical orientation to the generally horizontal orientation for side-entry stacking as illustrated. The individual undergarments U are compressed and conveyed by a compression conveyor to a position for stacking. The compression conveyor preferably includes a compression conveying drive, a plurality of compression rolls connected to the drive, and a plurality of belts slidably mounted to the rolls. During the driving of the rolls by the conveying drive, the belts compress and convey the individual undergarments along the path of travel P to the stacking means positioned downstream therefrom.

Side-entry stacking means, e.g., a side-entry stacker, of the stacking and packaging means is positioned downstream from the second separating means 180, the position orienting means, and the registration conveyor 155 for receiving a plurality of individual disposable undergarments U from the generally horizontal side-entry position and for stacking the plurality of disposable undergarments U into a predetermined stack. The side-entry stacker 190 is preferably positioned transverse the path of travel P so as to advantageously provide a shorter linear path of travel and shorter footprint for the apparatus 20. The stacker 190 preferably includes a base and a plurality of space-apart guiding arms rotatably mounted to the base. The side-entry stacker 190 can also include a stop member positioned to stop each of the plurality of compressed undergarments in a predetermined stop position after being conveyed by the registration conveyor 155. The spaced-apart guiding arms then rotate adjacent the predetermined stop position and individually lift each of the undergarments so that the undergarments are positioned between the guiding arms and transported to a stacker output position which provides stacks of undergarments. The stacker also preferably includes a controller for controlling the rotating guiding arms and for tracking and/or counting the individual undergarments U. The controller also allows an operator to set the number of undergarments to be arranged in the stacks for various sized or types of packaging or bagging.

After the plurality of individual undergarments U are stacked, the stack of undergarments U is compressed by a stacking compressor of the side-entry stacker and conveyed by a packaging conveyor of the stacking and packaging means 190 to a position for packaging or bagging. The packaging or bagging means of the stacking and packaging means 190 preferably includes a loader as understood by those skilled in the art which assists in the bagging of the stack of undergarments U by production process personnel such as designated undergarment baggers.

Preferably, a scrap/reject or bulk receiving source is also positioned between the undergarment separator 180 and the stacking and packaging 190. This scrap/reject or bulk receiving source also provides flexibility in the operation of the apparatus 20 as an outlet for a jam, a line down, or other operational problems that may arise.

Additionally, as an example of an alternative embodiment of the present invention, an apparatus according to the present invention can include leg forming means, e.g., a leg former, positioned downstream from the core forming means for forming a pair of leg openings in each of the plurality of undergarments U of the web W. This particular embodiment forms a brief product preferably used by an adult, but can also be used by a toddler. The leg forming means can include layer applying means for applying a continuous layer of non-woven material so as to underlie each of the plurality of individual undergarment cores C, leg elastic applying means positioned downstream from the layer applying means for applying leg elastic between the layer of non-woven material and the waistbands, and leg cutting means positioned downstream from the layer applying means for cutting the pair of leg openings in the layer of non-woven material. The side connecting means 150, e.g., a side sealer 160 as described above herein, according to this second embodiment, further connects the side peripheries of each of the plurality of undergarments U from the waistbands, along the side peripheries of the layer of non-woven material, and to each of the pair of leg openings.

As illustrated in FIGS. 1–10, and although other methods are illustrated as well, the present invention advantageously provides methods forming a connection of portions of a moving folded web W of disposable undergarments U. A method preferably includes registeringly conveying a folded web W of disposable undergarments along a predetermined path P of travel and connecting portions of the folded web W as the folded web W is conveyed along the predetermined path P of travel.

The method can also advantageously perform the step of registeringly conveying by positioning a folded web W between a first conveying belt 156 and a second conveying belt 157 so that each of the first and second conveying belts 156, 157 abuttingly contact the folded web W and driving the first and second conveying belts 156, 157 along the predetermined path P of travel. At least one of the first and second conveying belts 156, 157 preferably includes a first portion B1 having a first thickness and a second portion B2 having a second thickness. The first thickness B1 is preferably greater than the second thickness B2 so that a combination of the respective first portions B1, B2 of the first and second conveying belts,156, 157 is positioned to register and convey a waistband region W of the folded web W and a combination of the respective second portions B2, B4 is positioned to register and convey a core region C of the folded web W.

The method additionally can include the driving step including driving the first conveying belt 152 along a closed loop path and driving the second conveying belt 157 also along a closed loop path, e.g., at generally the same speed. The first and second conveying belts 156, 157 also can each include at least one opening 158, 159 formed therein. A first opening 158 of the first conveying belt 156 is advantageously positionally aligned with a first opening 159 of the second conveying belt 157 so as to define an open region of the first and second conveying belts 156, 157 so that portions of the moving web being registeringly conveyed by the belts extend within the open region (see, e.g., FIGS. 4 and 7).

The method can further include abuttingly contacting portions of the moving folded web W positioned in the open region with portions of an ultrasonic sealer 160 to thereby connect the portions of the moving web W positioned in the open region and separating the moving web W of disposable undergarments U into a plurality of individual disposable undergarments U. The separating step preferably include contacting the connected portions of the moving web W positioned in the open region with a separator 180 to thereby cuttingly separate the portions of the moving web positioned in the open region (see, e.g., FIGS. 8–9). The method can also still include folding cores C of each of the undergarments U of the moving web W along a first predetermined fold line L1 and side folding the folded cores C of a moving web of disposable undergarments U along a second predetermined fold line L2 so as to form the moving folded web W prior to the registeringly conveying step.

Another method of forming a connection of portions of a web w of disposable undergarments U preferably includes folding cores C of a web W of disposable undergarments U during travel along a predetermined path P, registeringly conveying the folded web W of disposable undergarments U along a predetermined path P of travel, connecting portions of the folded web W as the folded web W is conveyed along the predetermined path P of travel, and separating the folded web W of disposable undergarments U along the connected portions of the folded web W so as to form a plurality of individual disposable undergarments U.

This method can also perform the step of registeringly conveying by positioning a folded web W between a first conveying belt 156 and a second conveying belt 157 so that each of the first and second conveying belts 156, 157 abuttingly contact the folded web W and driving the first and second conveying belts 156, 157 along the predetermined path P of travel. The driving step can also include driving the first conveying belt 156 along a closed loop path and driving the second conveying belt 157 also along a closed loop path. The first and second conveying belts 156, 157 preferably each include at least one opening 158, 159 formed therein. A first opening 158 of the first conveying belt 156 is preferably positionally aligned with a first opening 159 of the second conveying belt 157 so as to define an open region of the first and second conveying belts 156, 157 so that portions of the folded web W being registeringly conveyed extend within the open region. This method can additionally include abuttingly contacting portions of the folded web W positioned in the open region with portions of an ultrasonic sealer 160 to thereby connect the portions of the folded web W positioned in the open region.

This method further can perform the separating step by contacting the connected portions of the folded web W positioned in the open region with a separator 180 to thereby cuttingly separate the portions of the folded web W positioned in the open region. The method can still further include side folding the folded cores C of the web W of disposable undergarments so as to form the moving folded web W prior to the registeringly conveying step.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed:

1. An apparatus for forming a connection of portions of a moving folded web of disposable undergarments, the apparatus comprising:

registration conveying means for registering and conveying a folded web of disposable undergarments moving along a predetermined path of travel, wherein said registration conveying means includes a first underlying conveying belt positioned to underlie the folded web, a second overlying conveying belt positioned to overlie the folded web, and driving means for driving the first and second conveying belts along the predetermined path of travel, and wherein said first and second conveying belts each include at least one opening formed therein, a first opening of said first conveying belt being positionally aligned with a first opening of said second conveying belt so as to define an open region of said first and second conveying belts so that portions of the moving folded web being registered by said registration conveying means extend within the open region; and web connecting means positioned adjacent said registration conveying means for connecting portions of the folded web as the folded web is conveyed along the predetermined path of travel.

2. An apparatus as defined in claim 1, wherein at least one of said first and second conveying belts includes a first portion having a first thickness and a second portion having a second thickness, the first thickness being greater than the second thickness so that the first portion is positioned to register and convey a waistband region of the moving folded web and the second portion is positioned to register and convey a core region of the moving folded web.

3. An apparatus as defined in claim 1, wherein said first underlying conveying belt travels along a closed loop path so that a first portion of be web connecting means is positioned within the closed loop path of said first conveying belt, and wherein said second overlying conveying belt also travels along a closed loop path so that a second portion of the web connecting means is positioned within the closed loop path of said second conveying belt.

4. An apparatus as defined in claim 1, wherein said web connecting means is positioned adjacent said registration conveying means for abutting contact of portions of said web connecting means with the moving web positioned in the open region of said registration conveying means to thereby conned the portions of the moving folded web positioned in the open region.

5. An apparatus as defined in claim 1, further comprising separating means positioned downstream from said web connecting means for separating the moving folded web of disposable undergarments into a plurality of individual disposable undergarments.

6. An apparatus as defined in claim 5, wherein said separating means is positioned adjacent said registration conveying means for contacting portions of the moving web positioned in the open region with said separating means to thereby cuttingly separate the portions of the moving web positioned in the open region of said registration conveying means.

7. An apparatus as defined in claim 1, further comprising core folding means positioned upstream from said registration conveying means for folding cores of each of the disposable undergarments of a moving web along a predetermined fold line and side folding means positioned upstream from said registration conveying means and downstream from said core folding means for side folding the folded cores of a moving web of disposable undergarments so as to form the moving folded web prior to entry into said registration conveying means.

8. An apparatus as defined in claim 1, wherein said web connecting means includes ultrasonic sealing means having at least one horn and at least one anvil positionally aligned with said at least one horn, and wherein said at least one horn and said at least one anvil are each positioned to travel with the registration conveying means when conveying the folded web downstream.

9. An apparatus for forming a connection of portions of a moving folded web of disposable undergarments, the apparatus comprising:
a registration conveyor positioned to register and convey a folded web of disposable undergarments moving along a predetermined path of travel, wherein said registration conveyor includes a first conveying belt positioned to abuttingly contact the folded web, a second conveying belt positioned to abuttingly contact the folded web, and at least one drive positioned to drive the first and second conveying belts along the predetermined path of travel, and wherein at least one of said first and second conveying belts includes a first portion having a first thickness and a second portion having a second thickness, the first thickness being greater than the second thickness so that the first portion is positioned to register and convey a waistband region of the moving folded web and the second portion is positioned to register and convey a core region of the moving folded web; and
an ultrasonic sealer positioned adjacent said registration conveyor to connectingly seal portions of the folded web as the folded web is conveyed along the predetermined path of travel, wherein said first conveying belt travels along a closed loop path so that a first portion of the ultrasonic sealer is positioned within the closed loop path of said first conveying belt, and wherein said second conveying belt also travels along a closed loop path so that a second portion of the ultrasonic sealer is positioned within the closed loop path of said second conveying belt.

10. An apparatus as defined in claim 9, wherein said first and second conveying belts each include at least one opening formed therein, a first opening of said first conveying belt being positionally aligned with a first opening of said second conveying belt so as to define an open region of said first and second conveying belts so that portions of the moving folded web being registered by said registration conveyor extend within the open region.

11. An apparatus as defined in claim 10, wherein said ultrasonic sealer is positioned adjacent said registration conveyor to abuttingly contact portions of said ultrasonic sealer with the moving folded web positioned in the open region of said registration conveyor to thereby connect the portions of the moving folded web positioned in the open region.

12. An apparatus as defined in claim 10, further comprising an undergarment separator positioned downstream from said ultrasonic sealer to separate the moving folded web of disposable undergarments into a plurality of individual disposable undergarments.

13. An apparatus as defined in claim 12, wherein said undergarment separator is positioned adjacent said registration conveyor to contact portions of the moving web positioned in the open region with said undergarment separator to thereby cuttingly separate the portions of the moving folded web positioned in e open region of said registration conveyor.

14. An apparatus as defined in claim 9, further comprising a core folder positioned upstream from said registration conveyor to fold cores of each of the disposable undergarments of the moving folded web along a predetermined fold line and a side folder positioned upstream from said registration conveyor and downstream from said core folder to side fold the folded cores of a moving web of disposable undergarments so as to form the moving folded web prior to entry into said registration conveyor.

15. An apparatus as defined in claim 9, wherein said ultrasonic sealer having at least one horn and at least one anvil positionally aligned with said at least one horn, and wherein said at least one horn and said at least one anvil are each positioned to travel with the registration conveyor when conveying the folded web downstream.

16. An apparatus for forming a connection of portions of a moving folded web of disposable undergarments, the apparatus comprising:
a registration conveyor positioned to register and convey a folded web of disposable undergarments moving along a predetermined path of travel, wherein said registration conveyor includes a first conveying belt positioned to abuttingly contact the folded web, a second conveying belt positioned to abuttingly contact the folded web, and at least one drive positioned to drive the first and second conveying belts along the predetermined path of travel, and wherein said first and second conveying belts each include at least one opening formed therein, a first opening of said first conveying belt being positionally aligned with a first opening of said second conveying belt so as to define an open region of said first and second conveying belts so that portions of the moving web being registered by said registration conveyor extend within the open region; and an ultrasonic sealer positioned adjacent said registration conveyor to connectingly seal portions of the folded web as the folded web is conveyed along the predetermined path of travel.

17. An apparatus as defined in claim 16, wherein said ultrasonic sealer is positioned adjacent said registration conveyor to abuttingly contact portions of said ultrasonic sealer with the moving folded web positioned in the open region of said registration conveyor to thereby connect the portions of the moving folded web positioned in the open region.

18. An apparatus as defined in claim 16, further comprising an undergarment separator positioned downstream from said ultrasonic sealer to separate the moving web of disposable undergarments into a plurality of individual disposable undergarments.

19. An apparatus as defined in claim 18, wherein said undergarment separator is positioned adjacent said registration conveyor to contact portions of the moving folded web positioned in the open region with said undergarment separator to thereby cuttingly separate the portions of the moving folded web positioned in the open region of said registration conveyor.

20. An apparatus as defined in claim 16, further comprising a core folder positioned upstream from said registration conveyor to fold cores of each of the disposable undergarments of the moving folded web along a predetermined fold line and a side folder positioned upstream from said registration conveyor and downstream from said core folder to side fold the folded cores of a moving web of disposable undergarments so as to form the moving folded web prior to entry into said registration conveyor.

21. An apparatus as defined in claim 16, wherein said ultrasonic sealer having at least one horn and at least one anvil positionally aligned with said at least one horn, and wherein said at least one horn and said at least one anvil are each positioned to travel with the registration conveyor when conveying the folded web downstream.

* * * * *